(12) United States Patent
Poirier et al.

(10) Patent No.: US 9,144,419 B2
(45) Date of Patent: Sep. 29, 2015

(54) SAMPLE INJECTION PORT FOR LAMINATED DEVICES

(75) Inventors: Michael Scot Poirier, Vista, CA (US); Andrew Moulds, Encinitas, CA (US)

(73) Assignee: Qualigen, Inc., Carlsbad, CA (US)

( * ) Notice: Subject to any disclaimer, the term of this patent is extended or adjusted under 35 U.S.C. 154(b) by 1010 days.

(21) Appl. No.: 13/125,733

(22) PCT Filed: Oct. 23, 2009

(86) PCT No.: PCT/US2009/061820
§ 371 (c)(1),
(2), (4) Date: May 17, 2011

(87) PCT Pub. No.: WO2010/048494
PCT Pub. Date: Apr. 29, 2010

(65) Prior Publication Data
US 2011/0300639 A1    Dec. 8, 2011

Related U.S. Application Data

(60) Provisional application No. 61/108,353, filed on Oct. 24, 2008.

(51) Int. Cl.
| G01N 1/10 | (2006.01) |
| B01L 3/00 | (2006.01) |
| A61B 10/00 | (2006.01) |
| B01L 3/02 | (2006.01) |

(52) U.S. Cl.
CPC ......... *A61B 10/0096* (2013.01); *A61B 10/0045* (2013.01); *B01L 3/0279* (2013.01); *B01L 3/0275* (2013.01); *B01L 2200/02* (2013.01); *B01L 2200/026* (2013.01); *B01L 2200/027* (2013.01); *Y10T 436/2575* (2015.01)

(58) Field of Classification Search
CPC . B01L 3/0275; B01L 3/0279; B01L 2200/02; B01L 2200/026; B01L 2200/027; A61B 10/0096; A61B 10/0045; Y10T 436/2575
See application file for complete search history.

(56) References Cited

U.S. PATENT DOCUMENTS

| 6,010,463 A | 1/2000 | Lauks et al. |
| 2004/0141880 A1 | 7/2004 | Handler et al. |
| 2008/0009061 A1 | 1/2008 | Goto et al. |
| 2010/0242634 A1* | 9/2010 | Hubbuch et al. ........... 73/863.23 |

FOREIGN PATENT DOCUMENTS

| CA | 2435789 | 1/2004 |
| WO | WO 2006116964 A2 * | 11/2006 |
| WO | 2007120816 | 10/2007 |

* cited by examiner

*Primary Examiner* — Christopher A Hixson
(74) *Attorney, Agent, or Firm* — Fish & Tsang LLP

(57) ABSTRACT

Contemplated diagnostic test containers and methods include an adapter configured to sealingly receive and retain a positive displacement pipette tip to so form a fluid-tight seal for the container during at least part of the diagnostic test. Most preferably, the entire container is flexible and the container and adapter are single-use disposable and are usable with known commercially available positive displacement pipette tips.

10 Claims, 2 Drawing Sheets

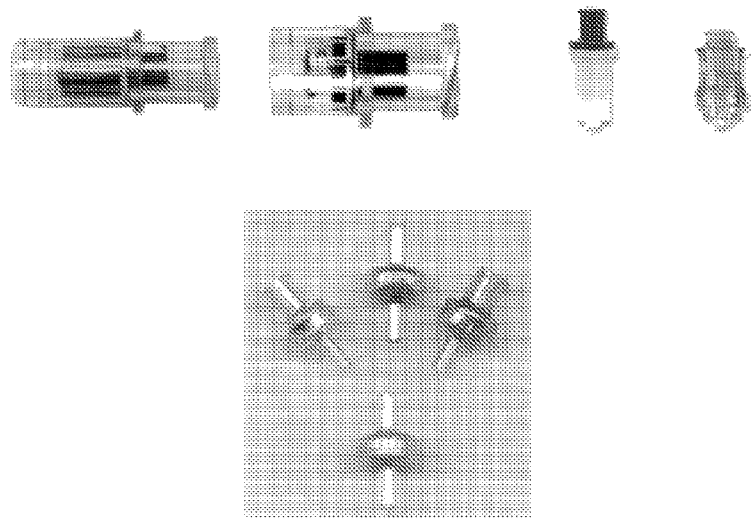
Prior Art Figure 1
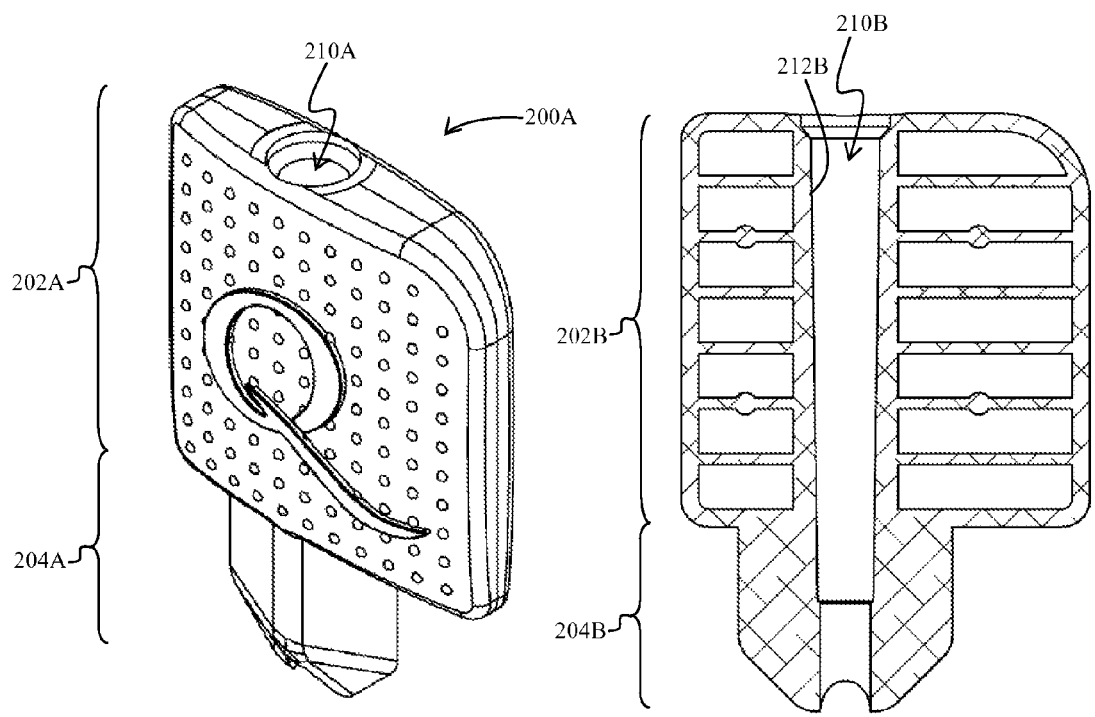
Figure 2A                    Figure 2B

SAMPLE INJECTION PORT FOR LAMINATED DEVICES

This application claims priority to our U.S. provisional application having Ser. No. 61/108,353, filed Oct. 24, 2008, which is incorporated by reference herein.

FIELD OF THE INVENTION

The field of the invention is adapters, and especially adapters for delivery of a fluid to a diagnostic device.

BACKGROUND OF THE INVENTION

Fluid containers and especially flexible fluid containers for medical test systems often have problems associated with backflow of fluids that were previously introduced into the container. In one known way to avoid backflow, the container is held in a fixed position after fluid introduction to avoid reverse fluid flow. However, maintaining a fixed position is often problematic where the containers must be moved or otherwise manipulated, and/or where the container is flexible. In such case, undesired introduction of air may further complicate the process.

In another known way to avoid backflow, check valves can be used at the point of fluid introduction, and examples of known check valves are shown in Prior Art FIGS. 1-3. However, check valves often add substantial expense to the cost of the container and impose additional production steps in manufacture. Still further, most known commercially available check valves have a relatively large diameter, which typically interferes with tight packing or rolling of the containers, thus negating at least some of the advantages provided by flexible and flat test containers. To overcome some of these difficulties with known check valves, luer lock unidirectional duck bill valves can be used as described in WO07/120816. This and all other extrinsic materials discussed herein are incorporated by reference in their entirety, and it is noted that where a definition or use of a term in an incorporated reference is inconsistent or contrary to the definition of that term provided herein, the definition of that term provided herein applies and the definition of that term in the reference does not apply. While such duck bill valves tend to reduce the space requirements, they generally necessitate relatively large sample volumes as the luer lock of the valve matingly engages with a syringe and so creates a relatively large dead space.

Alternatively, dedicated custom made filling devices may be implemented to reduce problems associated with backflow. However, such filling devices tend to be expensive, and require at least in some cases maintenance and/or trained personnel. Furthermore, such filling devices typically require special fixturing and/or tooling for sample fluid introduction and the retention of fluids in the sample compartment.

In addition to backflow problems associated with currently known filling devices and structures, additional problems arise, especially where the container is flexible and/or where the fluid volume to be introduced is relatively small (e.g., less than 1000 µl). Among other problems, flexible containers are often subject to compression and thus at risk of valve failure. Moreover, the internal dead space of most of the currently known filling devices can be as large or even larger than the sample volume that is to be introduced, which renders sample application inaccurate at best.

Therefore, even though numerous containers with filling devices are known in the art, all or almost all of them suffer from one or more disadvantages. Consequently, there is still a need for containers with filling devices through which fluid can be introduced in a relatively small volume while eliminating backflow and leakage.

SUMMARY OF THE INVENTION

The present invention is directed to devices and methods for introduction of fluid into containers, and especially into (preferably flexible) containers for diagnostic tests where an adapter has a channel sealingly engages with the outer surface of a positive displacement pipette tip. As the channel preferably terminates in the sample receiving compartment, and as the tip remains in the adapter during the use of the container, dead space is entirely avoided and the container remains sealed throughout the test due to the piston in the capillary of the tip and due to the sealing fit of the tip in the channel.

In one aspect of the inventive subject matter, an adapter usable in conjunction with a reagent container includes a housing that has a preferably continuous channel, wherein the channel has one end that is fluidly coupled to a sample receiving compartment of the container, and wherein the housing and the positive displacement pipette tip form a fluid-tight seal between the sample receiving compartment and a location outside of the container when the positive displacement pipette tip is removed from the pipette.

It is generally preferred that the adapter is permanently coupled to the container, and that the adapter and container are single-use disposable. Moreover, it is further preferred that the container has at least one flexible wall or that substantially the entire container is flexible, and that the adapter is rigid. Consequently, and particularly where the container is configured as a flat pouch, the thickness of the adapter in especially contemplated devices and methods is larger than a smallest thickness of the container. While all known positive displacement pipette tips are deemed suitable for use herein, it is especially preferred that the channel is configured to retain the positive displacement pipette tip where the positive displacement pipette tip has a rated volume of equal or less than 250 µl.

Consequently, in another aspect of the inventive subject matter, numerous (preferably flexible) test containers for diagnostic and other tests are contemplated that include one or more of the adapters contemplated herein.

Viewed from another perspective, the inventor contemplates a method of performing an analytic test in which a multi-compartment container is provided to which an adapter is coupled, wherein the adapter has a channel that is configured to sealably receive and retain a positive displacement pipette tip of a pipette, and fluidly couple a sample receiving compartment within the container with a location outside of the container. In such methods, a positive displacement pipette tip is inserted into the channel to deliver a sample fluid into the sample receiving compartment, wherein the positive displacement pipette tip forms a fluid-tight seal between the sample receiving compartment and a location outside of the container after the sample fluid has been delivered to the sample receiving compartment. The analytic test is then performed using the sample while the positive displacement pipette tip remains in the channel.

Where the container has at least one flexible wall, it is preferred that at least a portion of the sample receiving compartment is compressed (e.g., to move the sample into a different compartment) while the positive displacement pipette tip is in the channel. Most preferably, the channel is configured to retain the positive displacement pipette tip where the positive displacement pipette tip has a rated volume of equal or less than 250 µl, and it is generally preferred that the container and adapter are discarded after a single use. With respect to further parameters of the container and adapter, the same considerations as provided above apply.

Various objects, features, aspects, and advantages of the present invention will become more apparent from the following detailed description of preferred embodiments of the invention, along with the accompanying drawing.

BRIEF DESCRIPTION OF THE DRAWINGS

Prior Art FIG. 1 depicts various exemplary commercially available check valves.

FIG. 2A depicts a perspective view of an exemplary port according to the inventive subject matter.

FIG. 2B depicts a cross-sectional view of the exemplary port of FIG. 2A.

DETAILED DESCRIPTION

The inventor has discovered that sample addition to a container (diagnostic device or other container with one or more reagent compartments) can be performed in a conceptually simple and effective manner in which the sample fluid is introduced into the container via an adapter that sealingly engages with a positive displacement pipette tip by which the sample fluid is conveyed into the container. Therefore, where the adapter sealingly engages with the container, and where the sample has been introduced into the container, the entire container will remain fluidly sealed by virtue of the positive displacement pipette tip that remains in the adapter.

Among other benefits, it should therefore be appreciated that addition of relatively small sample volumes (e.g., of equal or less than 1000 µl, and more typically equal or less than 250 µl) into the reagent container can be realized without loss of sample fluid due to dead space within an otherwise present unidirectional valve mechanism. Thus, it is now also possible to add known quantities of small sample volume to such containers. Still further, as the piston of the positive displacement pipette tip remains in the capillary during and after use, the tip will also act as a seal (together with the inner surface of the channel that sealingly engages with the outside of the tip) that prevents backflow of the sample or other liquid from the container to a position outside of the container (and adapter). Consequently, it should be appreciated that contemplated methods and devices presented herein will advantageously solve numerous heretofore encountered problems while eliminating use of any moving part (and with that potential point-of-failure) in the fluid port.

FIG. 2A depicts one exemplary adapter 200A having a body portion 202A and an attachment portion 204A. Extending through the body 202A and attachment portion 204A is channel 210A that comprises a surface that typically has a frustoconical shape to so matingly engage with at least a portion of the outer surface of a positive displacement pipette tip (not shown; see FIGS. 3A and 3B). FIG. 2B depicts a cross sectional view of the adapter of FIG. 2A in which it can be seen that the body portion 202B and the attachment portion 204B are continuously coupled to each other, and in which the channel 210B extends through the body portion 202B and the attachment portion 204B. In the view of FIG. 2B, it is readily apparent that a portion 212B of the channel 210B has a shape that matingly engages with at least a portion of the outer surface of a positive displacement pipette tip (not shown; see FIGS. 3A and 3B).

Figure 3A:
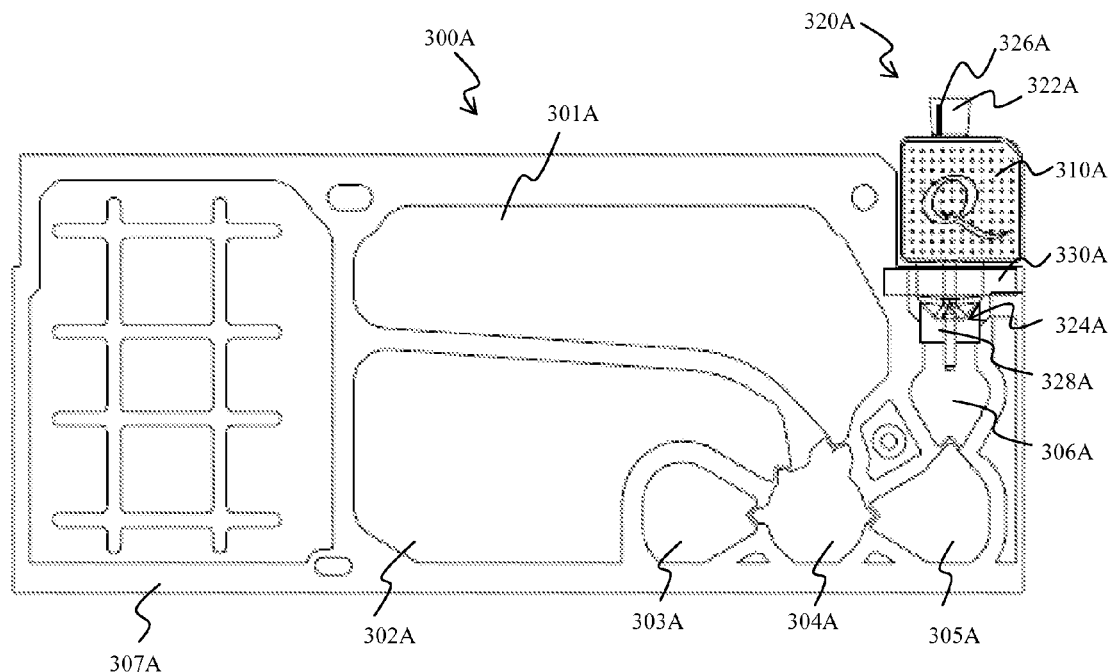
FIG. 3A depicts a top view of an exemplary diagnostic device with the exemplary port of FIG. 2A having a positive displacement pipette tip inserted.

FIG. 3A depicts an exemplary diagnostic test container 300A that has a plurality of compartments 301A-305A and a sample receiving compartment 306A that is fluidly coupled to the channel of the adapter 310A. As can be seen from this figure, the compartments are arranged such that fluid can be moved from one compartment to another in a bi-directional manner (e.g., using valves or a device that uses a plurality of actuators that compress portions between the compartments to so direct and/or block flow). Positive displacement pipette tip 320A remains inserted in the adapter 310A (piston 326A remains in the capillary 328A) after addition of the sample such that an upper portion 322A of the pipette tip remains at the outside of the adapter 310A and such that a lower portion 324A of the pipette tip extends into the sample receiving compartment 306A. In the example of FIG. 3A, the adapter 310A is coupled to the body of the container 307A via intermediary structure 330A that is sealingly coupled to the body 307A and adapter 310A. Most preferably, body 307A of the diagnostic test container 300A is formed from flexible sheets (typically made from polymeric materials) to allow for a flat and flexible configuration.

Figure 3B:
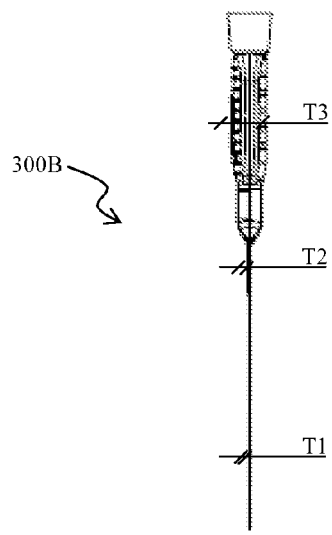
FIG. 3B depicts a side view of the exemplary diagnostic device of FIG. 3A.

A side view of the container of FIG. 3A is shown in FIG. 3B where the container 300B has a first thickness T1 that is typically determined by the thickness of the materials used to form the container (e.g., two laminated sheets of polymeric material) in addition to any reagent present in one or more of the compartments. Where the pipette tip extends into the sample receiving compartment, the thickness of the container may additionally (relative to T1) be determined by the thickness of the tip to a second thickness T2. Finally, the thickest portion of the device is at the adapter having thickness T3, wherein preferably T3>T2≥T1.

With respect to the container it should be appreciated that numerous containers are deemed suitable for use herein, and that the particular use and/or configuration of the container is not critical. However, it is noted that the advantages of using an adapter according to the inventive subject matter are particularly evident where the container has at least one flexible wall, and more preferably where substantially the entire container (at least 90% of each side of the container) is flexible. Thus, especially suitable containers include those having rigid walls, containers having a pair of inflexible plates with deformable blisters, and particularly containers that are formed from two flexible sheets of polymeric materials (which can advantageously be rolled, stacked, or otherwise tightly packed). Still further, suitable containers will preferably have more than one compartment, and especially preferred containers will have a sample receiving compartment and at least one more compartment that is pre-filled with a liquid reagent. Therefore, in most preferred aspects, the container will be a container that is suitable for a diagnostic test and will include at least one further compartment that has one or more optically clear walls to so allow light scatter, fluorometric, and/or colorimetric analysis of the content in the compartment.

The term "flexible" as used herein means readily deformable using moderate manual force (e.g., manual force similar to that used in a handshake). For example, a plastic film having a thickness of less than 1 mm (and more typically less than 0.1 mm) can be readily deformed to a roll or otherwise curved configuration by application of moderate manual force. In contrast, a metal plate having a thickness of 1 mm or more is not considered flexible as moderate manual force will not result in the same deformation. Furthermore, it should be noted that a flexible object need not necessarily regain its original configuration after the force is removed. The term "rigid" as used herein refers to the property of not being readily deformable using moderate manual force.

It is further contemplated that all known manners of forming a container are suitable for use herein. Similarly, it is contemplated that all known methods for forming one or more of the compartments are suitable for use herein. However, it is generally preferred that the compartments are formed using a heat and/or pressure process (e.g., use of heated platens, ultrasonic welding, etc.). As already noted before, it is generally preferred that at least some of the compartments are fluidly coupled to each other (and/or the sample receiving compartment). Thus, compartments will also include at least one opening through which fluid can enter and/or exit. The opening can include for example, a one-way valve (e.g., a "duck bill" valve or similar apparatus), a two-way valve, a thin wall or membrane that can be punctured by a defined amount of pressure, and any other method of regulating fluid flow. Further suitable container configurations, aspects, and uses are described in U.S. Pat. Nos. 6,426,230 and 6,300,138, both of which are incorporated by reference herein.

With respect to the adapter it is contemplated that the adapter comprises a preferably rigid housing with a continuous channel that has one end that is fluidly coupled to the sample receiving compartment of the container while the other end forms an opening to the outside of the adapter. Most typically, the housing is a separate entity, however, where desired, the housing may also be formed as an integral unit with the container. Moreover, it should be noted that the housing may have more than one channel to so provide multiple ports to one or more compartments within the container. Where desired, the channel opening (or entire channel) may be temporarily covered by a septum or lid or other closure to prevent or reduce contamination of the container contents and/or avoid spillage of contents from the container to the outside.

It is further generally preferred that the channel is a continuous channel that is shaped and dimensioned to accommodate at least part of the outer wall of a pipette tip (especially of a positive displacement tip). Consequently, it is contemplated that press fit will in most cases be sufficient to sealingly receive and retain the tip. However, additional implements include sealing materials, low-tack adhesives, etc. to increase retention of the tip. Alternatively, the channel may further comprise one or more deformable elements to provide a snap-fit with the pipette tip, or the channel may even have a threaded portion to threadably retain tip. Thus, the shape of the channel may vary considerably. However, it is typically preferred that the channel has a tapered portion that matingly engages with the pipette tip. Furthermore, it should be noted that the channel may be formed integrally, or be added as a separate element to the housing.

The upper end of the channel has generally any shape that is suitable to receive the tip, however, it is preferred that the outer end is shaped such that at least a portion of the upper end of the pipette tip is exposed above the adapter when the tip is fully inserted into the channel. Similarly, the lower end of the channel is preferably configured such that the lower end of the pipette tip protrudes into the sample receiving compartment when the tip is fully inserted into the channel. Alternatively, the adapter may be configured such that the channel extends into the sample receiving compartment. Still further, it is contemplated that the channel has a length such that at least 50%, more typically at least 60%, even more typically at least 70%, and most typically at least 80% of the length of the pipette tip is within the channel or adapter when the tip is fully inserted into the channel.

In still further aspects of the inventive subject matter, the adapter includes multiple channels that allow feeding of multiple distinct fluids into multiple distinct compartments. Multiple channels leading to the same sample receiving compartment may also be included to so accommodate different sizes of pipette tips. Alternatively, the adapter may also include a branched channel (e.g., with a three-way or higher valve) to allow use of a single opening at the outside while permitting fluid access to multiple compartments. Additionally or alternatively, the adapter may also provide a channel that is configured to (e.g., sealingly) receive implements other than a positive displacement tip, including various gauge needle cannulae, cone orifices, and any other instrument suitable to control filling of the container's compartments. In such case, the channel preferably comprises a flow control element.

It is further generally preferred that the housing of the adapter is permanently coupled to the body of the container. For example, in especially preferred aspects of the inventive subject matter, the adapter will have an attachment portion and a body portion, wherein the attachment portion is permanently coupled to the body of the container. Depending on the type of container, the attachment portion may be relatively flat and suitable for gluing or welding, or have a locking structure (e.g., luer lock) that can lockingly engage with the container. Therefore, it is generally preferred that the attachment portion protrudes from the body of the adapter and has a shape that facilitates insertion into and/or coupling to the body of the container. Moreover, it is noted that the housing and/or attachment portion may be directly coupled to the body of the container or via an intermediary element. Such intermediary element may sealingly engage with the body of the container and provide an opening that allows sealing insertion of the attachment portion into the intermediary element of the container. Therefore, all manners of coupling (permanent or removable) are deemed suitable so long as the channel provides a fluid path between the outside of the container and the sample receiving compartment or other internal compartment.

Consequently, all known methods of sealing an adapter to a container are deemed suitable for use herein and include applying heat (e.g., laminating), applying adhesive (e.g., glue), welding including ultrasonic welding, reacting chemicals, etc. Alternatively, the adapter may be releasably coupled to container, using any suitable fluid-tight coupling including for example, a luer coupling, a luer (lock) coupling, a screw-thread coupling, a friction coupling, or a clamp.

In one exemplary use (e.g., a method for filling a multi-compartment container with a sample receiving compartment), a positive displacement pipette tip that is coupled to a pipette is inserted into the channel of the adapter, wherein the channel sealably receives and retains the pipette tip. Thus, once the pipette tip is inserted into the adapter, a fluid-tight seal is created between the adapter and the pipette tip. The sample fluid is then injected from the tip into the container by depressing the pipette plunger which moves the pipette piston to the stop position and thus forces the sample fluid contained in the pipette tip into the container. Advantageously, while the piston is in the stop position, the sample fluid is prevented from flowing back into the pipette tip and out of the container. The pipette is then disconnected from the pipette tip, and the pipette tip together with the piston are left within the adapter. Consequently, it should be appreciated that a test may be performed in the container while the tip (and piston) remains in the container. Most preferably, at least one of the adapter and the container are single-use disposable (i.e., are discarded after single use). Positive displacement tips are well known in the art, and all of the known tips are deemed suitable for use herein. Howegver, it is generally preferred that the positive displacement pipette tip has a rated volume of equal or less than 1000 µl, more preferably equal or less than 250 µl, and most preferably equal or less than 100 µl.

Therefore, the inventors also contemplate a method of performing an analytic test in which a multi-compartment container is provided to which an adapter is coupled. Preferably, the adapter has a channel that sealably receives and retains a positive displacement pipette tip of a pipette, and that fluidly couples a sample receiving compartment within the container with a location outside of the container. In another step, a positive displacement pipette tip is inserted into the channel to deliver a sample fluid into the sample receiving compartment, wherein the positive displacement pipette tip forms a fluid-tight seal between the sample receiving compartment and a location outside of the container after the sample fluid has been delivered to the sample receiving compartment. The analytic test is then performed using the sample while the positive displacement pipette tip is in the channel. Most typically, at least a portion of the sample receiving compartment is compressed while the positive displacement pipette tip is in the channel to so move fluids within the multi-compartment container. One exemplary sample filling operation for a container with an adapter according to the inventive subject matter is shown in http://www.youtube.com/watch?v=R3cLmy7o5Oo.

Thus, specific embodiments and applications for improved sample injection ports for laminated devices have been disclosed. It should be apparent, however, to those skilled in the art that many more modifications besides those already described are possible without departing from the inventive concepts herein. The inventive subject matter, therefore, is not to be restricted except in the spirit of the present disclosure. Moreover, in interpreting the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A test device comprising:
an adapter having a body portion and an attachment portion, and a continuous channel extending through the body portion and the attachment portion;
a flexible reagent container having a sample receiving compartment, wherein the attachment portion is permanently coupled to the flexible reagent container such that the channel extends into the sample receiving compartment;
wherein a portion of the channel is configured to matingly engage an outer wall of the tip to sealably receive and retain a positive displacement pipette tip pipette, and the portion of the channel has a length of at least 50% of a length of the pipette tip;
wherein the housing and the positive displacement pipette tip are configured to form a fluid-tight seal between the sample receiving compartment and a location outside of the container when the positive displacement pipette tip is removed from the pipette; and
wherein the fluid-tight seal is formed by an outer wall of the positive displacement pipette tip and the channel.

2. The test device of claim 1, wherein the adapter and container are configured to be single-use disposable.

3. The test device of claim 1, wherein the adapter is rigid.

4. The test device of claim 1, wherein at least 60% of a length of the pipette tip is within the channel or adapter when the pipette tip is fully inserted into the channel.

5. The test device of claim 1, wherein a thickness of the adapter is larger than a smallest thickness of the container.

6. The test device of claim 1, wherein the container has a rigid portion that is configured to sealingly engage with the attachment portion of the adapter.

7. The test device of claim 1, wherein the channel is configured to retain the positive displacement pipette tip where the positive displacement pipette tip has a rated volume of equal or less than 250 µl.

8. The test device of claim 1 wherein the channel has a frustoconical shape.

9. The test device of claim 1 wherein the channel is configured such that a lower portion of the pipette tip extends into the sample receiving compartment.

10. The test device of claim 1 wherein the flexible container is formed from two laminated sheets of polymeric material.

\* \* \* \* \*